United States Patent [19]

Skatulla et al.

[11] Patent Number: 5,215,629
[45] Date of Patent: Jun. 1, 1993

[54] METHOD OF SEPARATING AROMATICS FROM A HYDROCARBON MIXTURE HAVING AN AROMATIC CONTENT

[75] Inventors: Luzian Skatulla, Mülheim; Hans-Christoph Schneider, Hattingen; Hans-Jürgen Vollmer, Essen, all of Fed. Rep. of Germany

[73] Assignee: Krupp Koppers GmbH, Essen, Fed. Rep. of Germany

[21] Appl. No.: 803,186

[22] Filed: Dec. 5, 1991

[30] Foreign Application Priority Data

Jan. 23, 1991 [DE] Fed. Rep. of Germany ....... 4101848

[51] Int. Cl.$^5$ ............................................. B01D 3/40
[52] U.S. Cl. ......................................... 203/22; 203/3; 203/58; 203/75; 203/78; 203/81; 203/DIG. 8; 203/DIG. 9; 585/808; 585/865
[58] Field of Search .................. 203/22, 3, 58, 78, 75, 203/81, DIG. 8, DIG. 9, 88; 585/807, 808, 860, 865, 837, 838

[56] References Cited

U.S. PATENT DOCUMENTS

| | | | |
|---|---|---|---|
| 2,168,570 | 8/1939 | Kraft | 203/27 |
| 2,993,844 | 7/1961 | Nijan | 203/22 |
| 3,639,497 | 2/1972 | Martel et al. | 203/25 |
| 4,048,062 | 9/1977 | Asselin | 585/834 |
| 4,081,355 | 3/1978 | Preusser et al. | 203/58 |
| 4,246,073 | 1/1981 | Umeda et al. | 203/25 |
| 4,278,505 | 7/1981 | Danulat et al. | 203/58 |
| 4,586,986 | 5/1986 | Preusser et al. | 203/22 |
| 4,751,338 | 6/1988 | Tabak et al. | 585/415 |

Primary Examiner—Virginia Manoharan
Attorney, Agent, or Firm—Michael J. Striker

[57] ABSTRACT

A process for separating an aromatic from a mixture containing also nonaroma includes distilling off the nonaromatics from the top of the extractive distillation column as a top product, drawing the aromatic and selective solvent from the extractive distillation column and subsequently separating the selective solvent from the aromatic in a separator column. The extractive distillation column is provided with a separate top product distillation column for recovery of a selective solvent residue from the separated nonaromatics. The entry hydrocarbon mixture is heated prior to admission to the extractive distillation column by an indirect heat exchange with selective solvent drawn from the separator column and heated to a temperature of from 130° to 150° C.

The heated entry hydrocarbon mixture is depressurized to form a liquid phase and a vapor phase and these phases are separately fed into the extractive distillation column, the vapor phase entry point being below the liquid phase entry point. The distillation conditions in the top product distillation column are adjusted so that a sump product is obtained with a solvent content of 1.5 to 2.5% by weight. The sump product of the top product distillation column is fed back into the extractive distillation column to provide a reflux to the top of the extractive distillation column.

1 Claim, 1 Drawing Sheet

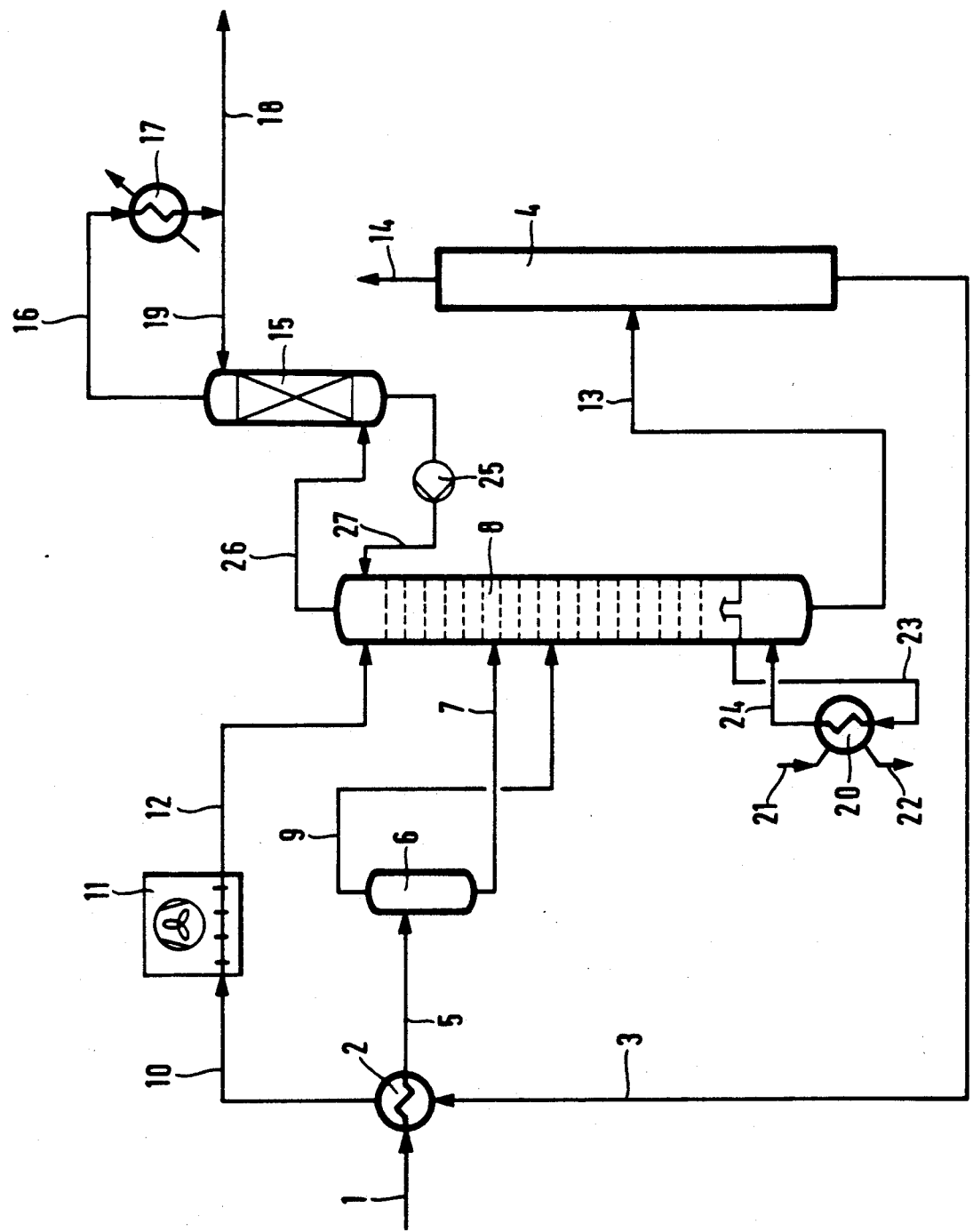

METHOD OF SEPARATING AROMATICS FROM A HYDROCARBON MIXTURE HAVING AN AROMATIC CONTENT

BACKGROUND OF THE INVENTION

The present invention relates to a method of separating an aromatic or aromatic compound from an entry hydrocarbon mixture having an aromatic content, i.e. containing a mixture of aromatic compounds, and containing nonaromatic components which can include paraffin, cycloparaffin, olefins, diolefins and organic sulfur compounds.

A method of separating an aromatic from an entry hydrocarbon mixture of this type is known. In this known method the separation occurs by an extractive distillation, in which N-substituted morpholine, whose substituents do not have more than seven carbon atoms, is used as selective solvent. The nonaromatic components of the entry hydrocarbon mixture are distilled off the head or top of an extractive distillation column, while the aromatic components are drawn off together with the selective solvent from the sump of the extractive distillation column. The top product is distilled in a separate top product distillation column for recovery of the solvent residue present in it.

The above-described method of obtaining aromatic compounds has been known for many years and has proven satisfactory in the intervening time in a number of different large scale plants, particularly in the case in which N-formyl morpholine is used as a selective solvent. Normally the sump product drawn from the extractive distillation column is conducted into a connected separating column, in which the aromatics contained in it are separated distillatively from the solvent. The solvent drawn from the sump of the separator column is fed back into the extractive distillation column for reuse. Up to now the solvent has been fed to and returned to the extractive distillation column at its head for various technical reasons, so that the top product still contains a certain solvent residue, which can amount to up to 2% by weight. Because of efficiency considerations and to obtain a top product, which is as pure as possible, it is essential that as much of this solvent in the top product be recovered as possible.

Up to now it was standard practice that top product from the extractive distillation column be conducted into a separate distillation column, in which the hydrocarbons of the top product were separated from the solvent. Since the hydrocarbons of the top product must have a solvent content less than 1 ppm, this distillative separation requires a highly expensive apparatus and a high energy consumption.

To decrease the high energy requirement, in German Published Patent Application 34 09 030 it has already been suggested that the distillative separation of the top product from the extractive distillation column be conducted under conditions such that the sump product obtained has a solvent content of from 20 to 75% by weight. Subsequently this sump product is separated in a separating vessel into a light phase and a heavy phase. The solvent rich heavy phase is returned to the extractive distillation column and the solvent poor light phase is fed to a top product distillation column. With this method of course the energy requirements for the purification of the top product are reduced. However, this still requires a separate column for the distillation of top product and also a separating vessel for the separation of heavier and lighter phase, which also means a not inconsiderable apparatus expense.

SUMMARY OF THE INVENTION

It is an object of the present invention to provide a process of the above-described type for obtaining an aromatic compound from an entry hydrocarbon mixture by extractive distillation method, in which the purity of the aromatic obtained from the extract is improved.

It is an object of the present invention to provide a method of the above-described type, in which the work-up of the top product obtained is made easier and more economical, without impairing the purity of the nonaromatics obtained from the method.

These objects and others, which will be made more apparent hereinafter, are attained in a method for separating an aromatic from an of arbitrary aromatic content and also containing nonaromatics, wherein the nonaromatics can include at least one member from the group consisting of paraffins, cycloparaffins, olefins, diolefins and organic sulfur-containing compounds. This extractive distillation method uses an extractive distillation column with a selective solvent consisting essentially of an N-substituted Morpholine having substituents each of which contain no more than seven carbon atoms. The extractive distillation column has a top, a sump and a solvent connector pipe through which the selective solvent is fed. The extractive distillation method includes distilling off the nonaromatics of the entry hydrocarbon mixture from the top of the extractive distillation column as a top product and drawing off an extractive distillation sump product containing the aromatic and the selective solvent together from the sump of the extractive distillation column, distilling the sump product of the extractive distillation in a separator column to obtain a heated solvent recovered portion and subsequently distilling the top product in a separate top product distillation column for recovery of a solvent residue present in the top product.

According to the invention, the method for separating the aromatic from the entry hydrocarbon mixture further comprises heating the entry hydrocarbon mixture to a temperature of 130° to 150° C. in an indirect heat exchange with the heated solvent recovered portion from a sump of the separator column to form a heated entry hydrocarbon mixture.

Advantageously, in a preferred embodiment of the invention, the heated entry hydrocarbon mixture is separated by depressurization of the mixture into a liquid phase and a vapor phase. The liquid phase is fed into the extractive distillation column at a liquid phase entry point which is above the vapor phase entry point for the vapor phase.

In another advantageous embodiment of the invention a top product distillation sump product with a solvent content from 1.5 to 2.5% by weight is obtained during the distilling of the top product in the top product distillation column by adjusting distillation conditions. Then the top product distillation sump product is fed back into the extractive distillation column to provide a reflux at the top of the extractive distillation column.

That means, in contrast to the method described in German Published Patent Application 34 09 030, separation of the sump product into a heavy phase and a lighter phase in a separate phase separator is avoided, so that expenses for apparatus are reduced. The method of the invention however is not obvious, because up to now it has always been accepted that a reflux in the extractive distillation column should be avoided or kept as small as possible to avoid an unnecessary dilution of the selective solvent by top product hydrocarbons fed back and formation of two liquid phases of separate density on the upper plates of the extractive distillation column.

Practical experience with the method of the invention has shown that the above fears did not materialize.

BRIEF DESCRIPTION OF THE DRAWING

The objects, features and advantages of the present invention will now be illustrated in more detail by the following detailed description, reference being made to the accompanying drawing in which:

The sole FIGURE is a flow chart showing an apparatus or plant performing the method according to the invention, in which only essential apparatus components are shown, but auxiliary devices, such as pumps, boilers, heat exchanges and measurement and regulatory devices, are not shown.

DETAILED DESCRIPTION OF THE PREFERRED EMBODIMENT

In the flow scheme shown in the drawing the entry hydrocarbon mixture is fed over the pipe 1 into the heat exchanger 2. A heated solvent recovered portion from the separator column 4 at a temperature of from 130° to 150° C., which is fed over the pipe 3, is also fed to the heat exchanger 2 so that an indirect heat exchange between the entry hydrocarbon mixture and the heated solvent recovered portion occurs. The heated entry hydrocarbon mixture is fed from the heat exchanger 2 into the separating vessel 6 over the pipe 5. In the separating vessel 6 it is depressurized to form a liquid phase and a vapor phase. The liquid phase is conducted over the pipe 7 into the central portion of the extractive distillation column 8. For example, the liquid phase can be introduced at the 24th plate (from the top) of an extractive distillation column of 55 plates total. Simultaneously the vapor phase is introduced over the pipe 9 under the supply location or solvent connector pipe for the liquid phase in the extractive distillation column 8. In the present case the feed of the vapor phase can occur 6 plates below the supply connection or feed pipe for the liquid phase. As has already been mentioned above, the method, if necessary, can also be performed, so that the heated entry hydrocarbon mixture coming over the pipe 5 from the heat exchanger 2 is fed directly into the central portion of the extractive distillation column 8.

In this extractive distillation column 8, the separation of the entry hydrocarbon mixture occurs with the solvent in a known way. The solvent coming from the heat exchanger 2 over the pipe 10 passes through the air cooler 11, in which it experiences the needed cooling so that subsequently its temperature is between 100° and 110° C. when it is feed back over the pipe 12 into the extractive distillation column 8. The solvent flows over the plates of this column downwardly so that it receives the vaporous aromatics. The liquid sump product, which comprises the solvent and the aromatics dissolved in it, is drawn over the pipe 13 from the extractive distillation column 8 and is conducted into the separator column 4, in which this sump product is broken up into its components. The details of structure of the separator column 4 need not be described in detail here, since the work up of the sump product of the extractive distillation is not the subject matter of the present invention. The aromatics are drawn as top products from the separator column 4 over the pipe 14, while the aromatic-free solvent collects in the sump of this column and can be fed over the pipe 3 to the heat exchanger 2.

The nonaromatic hydrocarbons of the entry hydrocarbon mixture, which form the top product phase, rise upwardly as a vapor in the extractive distillation column during the extractive distillation. So that the residual solvent can be removed from this nonaromatic hydrocarbon, the top product phase is drawn from the top of the extractive distillation column 8 and conducted over the pipe 26 to the so-called top product distillation column 15, which can be provided with plates or other suitable structures. The nonaromatic hydrocarbons released from the solvent residue escape as vapors from the top of the top product distillation column 15 and arrive over the pipe 16 in the cooler 17, in which those hydrocarbons are condensed. The main amount of liquid nonaromatics is supplied subsequently over the pipe 18 for further processing, while a smaller partial flow is returned over the pipe 19 to the head or top of the top product distillation column 15 as a reflux. The reflux is adjusted so that the obtained nonaromatics have the desired purity. Advantageously, it has been shown that one can work with a reflux ratio around 0.5. The sump product from the top product distillation column 15 coming down is drawn over the pipe 27 and fed back by pump 25 to the extractive distillation column 8, in which it is used as a reflux at the top of the column 8.

As already has been mentioned, in a preferred embodiment of the process of the invention the distillation conditions in the top product distillation column 15 are adjusted, so that the sump product of this column 15 is fed back with a solvent content of 1.5 to 2.5% over the pipe 27 to the extractive distillation column.

For heating the circulating boiler 20 is provided at the sump of the extractive distillation column 8. This boiler 20 heats the circulating sump product by an indirect heat exchange with steam. The pipes 21 and 22 serve for supply and removal of the steam and the pipes 23 and 24 for supply and delivery of the sump product from extractive distillation column 8. Understandably, additional auxiliary boilers can be arranged for additional column heating on the extractive distillation column 8. However since the column heating is not the subject matter of the present invention, these features are not described in detailed herein.

The unexpectedly improved efficiency of the method of the invention is proven by the following tests described herein in the following. A pyrolyzed benzene was used as an entry hydrocarbon mixture. The throughput capacity of the plate was about 14 600 kg/h. In part a) of the experimental series (experiment 1) the purity of the top product was determined in a separate distillation column according to the conventional method. In part b) in experiment 2 for testing the method of the invention the heated hydrocarbon mixture was conducted directly into the extractive distillation column. In experiment 3 the heated entry hydrocarbon mixture was broken up into a liquid and a vapor phase and both phases separated from teach other were conducted into the extractive distillation column. The experimental results are shown in the following Tables.

TABLE I

EXTRACTIVE DISTILLATION OF PRIOR ART METHOD

| Exper. No. | Inlet Temp. Entry Prod. °C. | Entry Plate Vapor/ Liquid (frm top) | Nonaromatics in Benzene ppm | Solvent in nonarom. (top product) ppm | Input Energy Gcal/h |
|---|---|---|---|---|---|
| EXP. 1 | 80 | 24 | 170 | $3 \times 10^{-3}$ | 1.806 |

TABLE II

EXTRACTIVE DISTILLATION ACCORDING TO THE INVENTION

| Exper. No. | Inlet Temp. Entry Prod. °C. | Entry Plate Vapor/ Liquid (frm top) | Nonaromatics in Benzene ppm | Solvent in nonarom. (top product) ppm | Input Energy Gcal/h |
|---|---|---|---|---|---|
| EXP. 2 | 130 | 24 | 123 | $<3 \times 10^{-3}$ | 1.803 |
| EXP. 3 | 130 | 30/20 | 98 | $<3 \times 10^{-3}$ | 1.803 |

The present experimental results show clearly that by using the method of the invention a clearly improved purity of the product benzene can be obtained without higher energy requirements than previously required and without a deterioration of the purity of the obtained nonaromatics. Since in this case a phase separation of the sump product of the top product distillation column in a separate phase separator can be avoided, a clear saving in apparatus and maintenance cost however has been obtained.

While the invention has been illustrated and as embodied in a method of separating an aromatic compound from a hydrocarbon mixture having an aromatic content, it is not intended to be limited to the details shown described, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

We claim:

1. In a method for separating an aromatic from an entry hydrocarbon mixture having an aromatic content and containing nonaromatics, by an extractive distillation method using an extractive distillation column with a selective solvent, the selective solvent consisting essentially of an N-substituted Morpholine having substituents each of which contain no more than seven carbon atoms and the extractive distillation column having a top, a sump and a solvent connector pipe through which the selective solvent is fed into the extractive distillation column, the extractive distillation method including distilling off the nonaromatics of the entry hydrocarbon mixture from the top of the extractive distillation column and drawing off a sump product containing the aromatic and the selective solvent from the sump of the extractive distillation column, distilling the sump product of the extractive distillation column in a separator column to obtain a heated solvent recovered portion from the separator column and, after the distilling off, distilling the top product of the extractive distillation column in a separate top product distillation column for recovery of a solvent residue present in the top product, the improvement comprising the steps of heating the entry hydrocarbon mixture to a temperature of 130° C. to 150° C. in an indirect heat exchange with the heated solvent recovered portion from the separator column to form a heated entry hydrocarbon mixture; depressurizing the heated entry hydrocarbon mixture to form a liquid phase and a vapor phase; feeding the liquid phase into the extractive distillation column at a liquid phase entry point; feeding the vapor phase into the extractive distillation column at a separate vapor phase entry point, the vapor phase entry point being below the liquid phase entry point; and adjusting distillation conditions in the top product distillation column so that a sump product of the top product distillation column is obtained with a solvent content of 1.5 to 2.5% by weight during the distilling of the top product in the separate top product distillation column, and feeding back the sump product of the top product distillation column into the extractive distillation column to provide a reflux to the top of the extractive distillation column.

* * * * *